United States Patent [19]

Klein

[11] 4,046,616
[45] Sept. 6, 1977

[54] AUTOMATIC ASSEMBLY APPARATUS OF SYRINGES

[75] Inventor: Edward Klein, Montreal, Canada

[73] Assignee: V-Mark Automation Ltd., Canada

[21] Appl. No.: 722,595

[22] Filed: Sept. 13, 1976

[51] Int. Cl.² .................... B32B 31/00; B65C 11/04
[52] U.S. Cl. .................................. 156/559; 156/578
[58] Field of Search ............... 156/559, 578, 356, 357

[56] References Cited

U.S. PATENT DOCUMENTS

| 2,693,843 | 11/1954 | Magnus et al. | 156/578 |
|---|---|---|---|
| 3,354,012 | 11/1967 | Forman et al. | 156/578 |
| 3,873,400 | 3/1975 | Tsuchida | 156/578 |

*Primary Examiner*—Douglas J. Drummond
*Attorney, Agent, or Firm*—Diller, Brown, Ramik & Wight

[57] ABSTRACT

The invention relates to an automatic assembly apparatus for assembling devices from a plurality of parts. The apparatus uses both continuous motion, for assembly, and reciprocal motion, for processing. The apparatus includes a sub-assembly station for assembling sub-assemblies from at least two of the parts and a processing station for processing a third one of the parts. The sub-assemblies and the processed parts are then brought to a main assembly station where they are assembled with the remaining of the parts to form an assembled device. In the embodiment illustrated, the apparatus is used to assemble syringes. At the processing station, the syringe barrels are cleansed and lubricated, and at the sub-assembly station the plunger tips are mounted on the plungers. The sub-assembly and the processed barrels are then brought to a main assembly station where they are assembled with needle arrangements to form an assembled syringe. In the preferred embodiment, the assembly station and the sub-assembly station are made of rotary drums having vertical slots equally spaced around the peripheries thereof to carry the various parts.

3 Claims, 10 Drawing Figures

AUTOMATIC ASSEMBLY APPARATUS OF SYRINGES

BACKGROUND OF THE INVENTION

I. Field of the Invention

This invention relates to an automatic assembly apparatus. More specifically, this invention relates to such an apparatus which combines continuous motion assembly and reciprocating motion processing.

II. Description of the Prior Art a. General

It is known in the art to use reciprocating motion processing apparatus, and it is also known to use continuous motion assembly in automatic assembly apparatus. However, reciprocating motion is only used in some such apparatus whereas continuous motion assembly is only used in other apparatus. There is no apparatus known to applicant which uses both types of motion to take advantage of the unique advantages offered by each.

Continuous motion assembly offers the advantage of high assembly speed. However, if processing such as filling or cleansing or coating operations is required, complicated moving parts would be necessary if these operations were to be carried out under continuous motion. It is therefore advantageous to carry these operations out under reciprocating motion.

Continuous motion assembly apparatus presently available is used mainly for the purpose of assembling two or three parts at a main assembly station. Such machines do not include sub-assembly stations for assembling and feeding sub-assemblies to a main assembly station, so that presently available machines are useful only for automatically assembling only very simple items with a small number of parts. In addition, continuous motion assembly machines will normally use a push rod mechanism to push one part onto or into another. The idea of using a cam acting directly on a part to push that part into or onto another part has not been embodied in any continuous motion assembly machines known to applicant.

b. Prior Art Patents

The following patents are representative of the art relating to automatic assembly apparatus of both the continuous motion and reciprocating motion types. Illustrated are general approaches to automatic assembly as well as specific features of the apparatus such as conveyors, hoppers, hopper to assembly station tracks using different orienting means, etc.

U.S. Pat. No. 3,750,256

This patent relates to a machine for mounting an insert 30 into a cap 32. It is, however, contemplated for using the machine for assembly of other nesting parts. The machine includes a carrousel 34 having a lower receptacle 94 for receiving the insert 30 at station A (see FIG. 3) An upper receptacle 91 receives the cap 32 at station B. A plunger tip 74 of plunger 60 (see FIG. 4) is inserted into the insert 30, thus checking for the presence of the insert 30 in the lower receptacle 94. In advancing from station A to station B, the plunger 60 lifts the insert 30 up and over the cap 34 which arrives at receptacle 90 in station B. The insert is then mounted in the cap at station D. This patent is of interest in that the plunger 60 is used as a safety check mechanism and if there is no insert 30 in the receptacle 94, the cap which arrives at the receptacle 90 will be discarded. If the insert is present, but the cap is not, this will be detected by the beam 142 (see FIG. 3) which in effect measures the height of the arriving part. As can be seen, with only an insert, the insert will slide under the bar 142 and be discarded.

U.S. Pat. No. 2,698,478

This patent teaches an automatic machine for inserting plungers into glass tubes. The plungers are conveyed on a wheel 10, and the tubes on a wheel 20, and, as can be seen in FIGS. 4 and 5, the two wheels meet at the assembly station. When the two wheels meet, the plunger drops into a groove in the wheel 20 which groove also carries the tube, so that the plunger is in position to be inserted into the tube. FIGS. 6, 7 and 8 show how the plungers are pushed into the tube by push rods 50. The plungers are actuated by a cam 60 as can be seen in FIG. 1.

U.S. Pat. No. 2,604,692

This patent was selected for its showing of an orienting means for orienting the apertured discs 12. As can be seen in FIG. 1, the orienting means consists of a flat plate at the bottom of the chute 18.

U.S. Pat. No. 3,588,985

This patent was selected as it relates to an apparatus for inserting a plunger and piston into a barrel of a hypodermic needle syringe. In the particular needle, there is a screw fit between the plunger and the piston, and the piston is rotated to screw it into the plunger (see FIGS. 7 to 11). The patent was also selected as it shows orienting means in chute 18 which consists of rails for engaging flanges K of the plunger.

U.S. Pat. No. 3,597,826

This is a patent by the same inventor as the inventor of U.S. Pat. No. 3,588,985. The machine in this patent is almost identical to the machine in the other patent except that in this patent, it is the syringe, rather than the plunger which is rotated.

U.S. Pat. No. 3,564,693

This patent relates to a conveyor for an automatic assembly machine with orienting means 18 for orienting the parts 16.

U.S. Pat. No. 2,183,600

This patent relates to a conveyor for providing aligned caps and rings to an assembly apparatus. Of interest here is the fact that the caps and rings are aligned in the conveyor.

U.S. Pat. No. 2,333,940

This was selected as an example of hopper and chute arrangements which are known in the prior art.

U.S. Pat. No. 2,996,105

This patent was also selected because it illustrates as assembly machine for hypodermic needles.

U.S. Pat. No. 1,947,610

This patent teaches a transfer mechanism for transferring a glass part from a mould to a conveyor.

U.S. Pat. No. 3,141,278

This patent is of interest with respect to its teaching of a timing star 9. The timing star transfers only one article at a time.

U.S. Pat. No 3,328,873

This is a further patent which teaches the use of a conveyor for presenting aligned caps and liners to an assembly apparatus.

STATEMENT OF THE INVENTION

It is an object of the invention to provide an automatic assembly apparatus which uses both continuous motion assembly and reciprocating motion processing.

It is a further object of the invention to provide such an apparatus which includes at least one sub-assembly station.

It is a further object of the invention to provide such an apparatus wherein a cam inter-acts directly with one or more parts to push these one or more parts onto or into other parts.

In accordance with the invention an automatic assembly apparatus for assembling devices from a plurality of parts comprises: a sub-assembly station comprising means for assembling sub-assemblies each comprising at least two of said parts; a processing station comprising means for processing at least a third one of said parts; a main assembly station comprising means for assembling all of said parts including said sub-assemblies and said processed parts; means for feeding said main assembly station with said sub-assemblies from said sub-assembly station; means for feeding said processed parts from said processing station to said main assembly station; characterized in that said means for assembling sub-assemblies and said means for assembling all of said parts are adapted to perform the assembling in a continuous motion assembly process; and in that said means for processing is adapted to perform said processing in a reciprocal motion process.

The main assembly station preferably comprises a rotary drum movable in a first direction; a first carrying means on said drum disposed over a portion of the height of said drum and along the entire periphery thereof, and rotating with the motion of said drum, said first carrying means comprising a plurality of equally spaced first vertical slots extending over the entire periphery of said drum, each said slot being adapted to receive and carry a respective first part therein; a first camming surface disposed over said first carrying means and sloping in a downward direction, said first camming surface being fixed relative to the motion of said first carrying means, said first camming surface abutting the tops of the first parts to move said first part downwardly when the drum is rotating in said first direction; a second carrying means on said drum below said first carrying means and disposed along the entire periphery of said drum, and rotating with the motion of said drum, said second carrying means comprising a plurality of equal spaced vertical slots equal to the plurality of said first slots, respective ones of said first slots being aligned with respective ones of said second slots, said second slots being adapted to receive and carry second parts therein; a rod carrying means on said drum below said second carrying means and disposed along the entire periphery of said drum, and rotating with the motion of said drum, said rod carrying means comprising a plurality of rods, movable vertically in said rod carrying means, said plurality of rods being equal to the plurality of said second slots, respective ones of said rods being aligned with respective ones of said second slots; and a second camming surface disposed below said rod carrying means and sloping in an upward direction, said second camming surface being fixed relative to the motion of said rod carrying means, said second camming surface abutting the bottom ends of said rods, the top ends of said rods engaging respective ones of said second parts, whereby, as the drum rotates in the one direction, said rods are moved upwardly by said second camming surface, and said second parts carried by said second surface are moved upwardly by said rods.

The sub-assembly station preferably comprises a rotary drum movable in a first direction; a plurality of equally spaced vertical slots disposed around the periphery of said drum, each of said slots being open at the top end thereof and closed at the bottom end thereof; first means for providing a first part to the top end of each one of said slots as said slots are adjacent said first means as the drum rotates in the one direction; second means, downstream of said first means in the first direction, for providing a second part at the bottom end of each slot and beneath each first part, to each one of said slots as said slots are adjacent said second means as the drum rotates in the one direction; camming means, being fixed relative to the motion of said drum and being disposed downstream of said second means in said first directiontion, said camming means sloping downwardly in said first direction and being disposed over said slot means to engage the top ends of said first parts to thereby move said first parts downwardly as said drum moves in said first direction; whereby respective ones of said first and second parts and joined to one another.

When the parts to be processed comprise cylindrical parts, the apparatus includes means to advance said cylindrical parts to said station in start-stop motion; said processing means comprising reciprocating means adapted to be inserted in the interior of said cylindrical parts and withdrawn therefrom during the stop part of said stop and start motion. The means for feeding will include orienting means for appropriately orienting their respective parts.

In the described embodiment, the apparatus is used for automatically assembling syringes, each said syringe comprising; a plunger having a stem, a top flanged end, and a bottom tip receiving end; a tip for mounting on said tip receiving end; a cylindrical barrel having a top flanged end and a bottom needle arrangement receiving end, said barrel receiving said plunger and tip in the interior thereof; and a needle arrangement for mounting on said needle arrangement receiving end; said apparatus comprising; a sub-assembly station for mounting said tip on said plunger including a first rotary drum having a plurality of equally spaced vertical slots disposed around the periphery thereof, each said slot being open at the top end thereof and closed at the bottom end thereof, means for rotating said drum in a first direction, means for providing plungers to said drum to be inserted at the top ends of respective slots one at a time, said plungers being inserted in said slots with the top ends of said plungers being adjacent the top ends of the respective slots and the plunger stems extending downward in the slot, a gap being provided in said slot between the tip receiving end and the bottom of each respective slot, means disposed downstream, in said first direction, of said means for providing plungers, for providing tips in the gaps at the bottom ends of the slots one at a time, a camming surface disposed downstream, in said first direction, of said means for providing tips, and located at the top end of said drum to engage the flanged top ends of the plungers as the drum rotates in said first direction, said cammed surface being sloped downwardly in the first direction, whereby the plungers are forced downwardly as they pass the camming surface, to force the tip receiving ends into the tips to mount the tips on the plunger and provide a plunger and tip arrangement; a processing station for cleansing and lubricating said barrels comprising elongated first means connected to a source of cleansor, said elongated first means being movable by vertically upwardly and vertically downwardly first moving means, elongated second means connected to a source of lubricant, said elongated second means being movable by vertically upwardly and vertically downwardly second moving means, and stop and start moving means to moving said barrels to said processing station such that, one barrel is disposed under said elongated first means and another barrel is disposed under said elongated second means, during each stop condition, whereby, during each stop condition the elongated first means is inserted in said one barrel and withdrawn from said one barrel cleansing said one barrel during the insertion and withdrawal of said elongated first means, said elongated first means being inserted in said one barrel after the start of a stop condition and being withdrawn from said one barrel before the start of the following start condition, and whereby, during each stop condition the elongated second means is inserted in said other barrel and withdrawn from said other barrel lubricating said other barrel during the insertion and withdrawal of said elongated second means, said elongated second means being inserted in said other barrel after the start of a stop condition and being withdrawn from said other barrel before the start of the following start condition; a main assembly station for assembling the plunger and tip arrangements, the processed barrels and the needle arrangement comprising; a secondary rotary drum having means for rotating said drum in an assembly direction; said secondary rotary drum having an upper carrying surface for receiving plunger and top arrangements from said sub-assembly station at a first point on said second rotary drum, said upper carrying surface being movable with said second rotary drum and comprising a plurality of equally spaced vertical plunger and tip arrangement carrying slots disposed around the periphery of said second rotary drum; an upper camming surface disposed over the top of said upper carrying surface and sloping downward in said assembly direction, said upper camming surface being fixed relative to the motion of said second rotary drum, said upper camming surface engaging the top flanged ends as said upper surface moves past the upper camming surface in the assembly direction whereby to force the plunger and tip arrangements downwardly; a center carrying surface for receiving processed barrels from said processing station at a second point on said second rotary drum downstream of said first point, said center surface comprising a plurality of equally spaced vertical barrel carrying slots disposed around the periphery of the second rotary drum, said center carrying surface being movable with said second rotary drum; a lower carrying surface for receiving said needle arrangements at a third point on said second rotary drum downstream of said second point, said lower carrying surface comprising a plurality of vertical needle arrangement carrying slots disposed around the periphery of said second rotary drum, said lower surface being movable with said second rotary drum; the plurality of said vertical plunger and tip arrangement slots being equal to and aligned with respective ones of the plurality of vertical barrel carrying slots and the plurality of needle arrangement carrying slots; glue dispenser means located adjacent said second rotary drum at a fourth point thereof downstream of said third point, for applying glue to each needle arrangement receiving end of each barrel as each barrel reaches said fourth point; a rod carrying means disposed around the periphery of said second rotary drum and beneath said carrying surface and movable with said second rotary drum, said rod carrying means comprising a plurality of vertical rods movable up and down in said rod carrying means, the plurality of rods being equal to and aligned with respective ones of the plurality of needle arrangement carrying slots; a lower camming surface disposed below said rod carrying means and sloping upward in said assembly direction, the lower carrying surface being fixed relative to the motion of said second rotary drum, the lower camming surface engaging the bottom ends of said rods to force said rods upwardly; the top end of said rods engaging the bottom ends of respective ones of said needle arrangements, whereby the needle arrangements are forced upwardly as the rods are forced upwardly; constant pressure applying means in said lower camming surface disposed downstream of said glue dispenser means and adapted to apply constant pressure, through each said rods, to a respective needle arrangement, as it is being mounted on a respective barrel; whereby, as said second rotary drum moves in the assembly direction, each plunger and tip is inserted into a respective processed barrel, glue is applied to each barrel at the needle arrangement receiving end thereof, each needle arrangement is mounted on a respective barrel at the glued needle receiving end thereof, and constant pressure is applied to each needle receiving end to fix it to its respective barrel, to provide completely assembled syringes.

The apparatus further includes a first container for said plungers; a second container for said plunger tips; a third container for said barrels; a fourth container for said needle arrangements; a first track for carrying said plungers to said sub-assembly station at one point thereof, said first track comprising rails for orienting said plungers in a vertical attitude with the flanged ends at the top; a second track for carrying said plunger tips to said sub-assembly station downstream of said one point thereof, said second track comprising rails for orienting said plunger tips; a third track for carrying said barrels to said processing station, and a fourth track for carrying processed barrels to the second point on said second rotary drum, said third and fourth tracks comprising rails for orienting said barrels in a vertical attitude with the flanged ends thereof at the top; and a fifth track for carrying said needle arrangements to the third point on said second rotary drum, said fifth track comprising rails for orienting said needle arrangements.

When each of said tips comprises a flange at both ends thereof, one of each said flanges being a wide flange and the other one of each said flanges being a narrow flange, the rails on said second track comprise; a first pair of notches wide enough to pass the narrow flanges but not the wide flanges; a second pair of notches wide enough to pass the wide flanges; the first pair of notches being spaced from the second pair of notches by a distance substantially equal to the length of the tips; a first source of pressurized air to provide a vertically downwardly directed stream of air, disposed over the track adjacent the first pair of notches; and a second source of pressurized air, downstream of said first source, to provide a stream of air across said second track.

BRIEF DESCRIPTION OF DRAWINGS

The invention, together with specific features thereof, will be more particularly described in the following together with the accompanying drawings in which.

DESCRIPTION OF PREFERRED EMBODIMENTS

Like reference numerals in all FIGS. refer to the same parts.

In the illustrated embodiment, the apparatus is shown adaptable to assembling syringes. It will be obvious to one skilled in the art that the same principles as illustrated herein can be used in apparatus used for assembling other devices.

Figure 1:
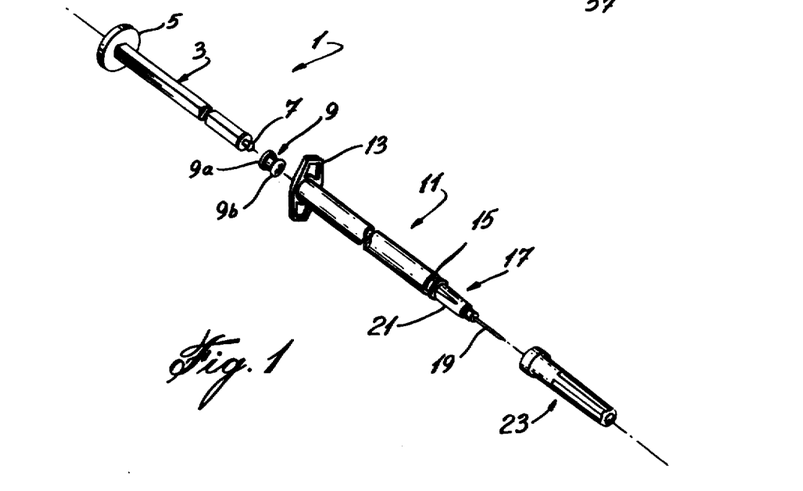
FIG. 1 is an exploded view of a syringe which the inventive apparatus is used to assemble.

In order to better appreciate the operation of the novel apparatus, a brief description of the syringe which can be assembled with the apparatus follows. Referring to FIG. 1, the syringe consists of a plunger, indicated generally at 1, and including a plunger stem 3 having a flanged top end 5 and a plunger tip receiving means 7 at the bottom end thereof. Plunger tip 9 is made of a resilient material such as rubber and includes a longitudinal cylindrical opening therethrough. The diameter of the opening is less than the diameter of plunger tip receiving means 7 so that the plunger tip will resiliently grip the means 7 to thereby be retained on the plunger stem.

The plunger stem, with the tip mounted at the bottom end thereof, is inserted into cylindrical barrel 11, which includes a flanged top end 13 and a needle arrangement receiving means 15 at the bottom end thereof. Needle arrangement 17, which includes needle 19 and cup retainer 21, is mounted on the means 15 by inserting 15 into the cup 21. The means 15 is retained in the cup by glue. The needle arrangement may be covered by cap 23. In the embodiment including the cap, the needle arrangement and cap are pre-assembled before being fed to the assembly apparatus in accordance with the illustrated embodiment.

As will be seen from the foregoing, the apparatus will require means for providing glue, and further means for mounting the cup on the means 15 (or inserting the means 15 into the cup 21). In the apparatus described herein, the needle arrangement and pre-assembled cap 23 are mounted on the barrel 11 after the plunger and tip are inserted into the barrel.

Figure 2:
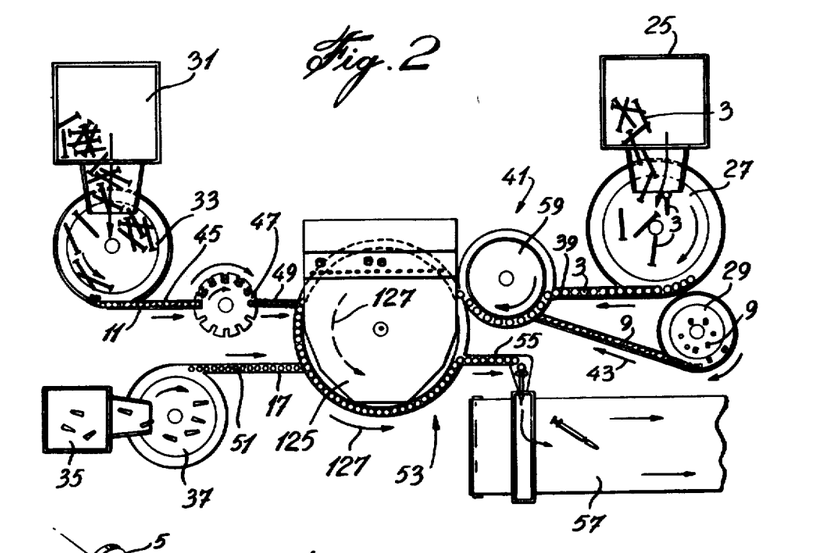
FIG. 2 is a somewhat schematic diagram of the inventive apparatus.

Referring now to FIG. 2, the apparatus includes a plunger container 25 which feeds a plunger hopper means 27. Plunger tips 9 are fed from container and hopper means 29, and barrels 11 are supplied from container 31 to hopper means 33. Finally, needle arrangements 17 are fed, from container 35 to hopper means 37.

Hopper means 27 is connected via track 39 to sub-assembly station 41 snd track 43 leads from hopper 29 to the same sub-assembly station. As will be seen below, the plunger tips are mounted on the plungers at station 41 and the assembled plungers and tips are then fed to the main assembly station 53.

Track 45 leads from hopper 33 to a processing station such as the barrel cleaning and coating station 47. As will be described below, the barrels are cleansed and the inside thereof coated at this station. The barrels are processed by reciprocating motion and moved through this station by start-stop motion rather than continuous motion as in the remainder of the apparatus. The cleansed and coated barrels are then carried on track 49 to the main assembly station 53.

Needle arrangements 17 are carried to the main assembly station 53 by track 51, and the entire syringe is assembled at the main assembly station and then dispensed by dispensing means 55 to container or conveyor belt 57.

Turning now to FIGS. 3 to 6, the sub-assembly 41 comprises a rotating drum 59 which rotates in the direction of the arrow 60. The drum includes a plurality of semi-cylindrical slots which are evenly spaced around the periphery of the drum. Each slot extends from the top of the drum where the slot is open, substantially to the bottom of the drum. The bottom end of each slot is closed by the bottom of the drum. Guide 62 retains the plunger stems in place in the respective slots of the drum.

Figures 3, 4, 5, 6:
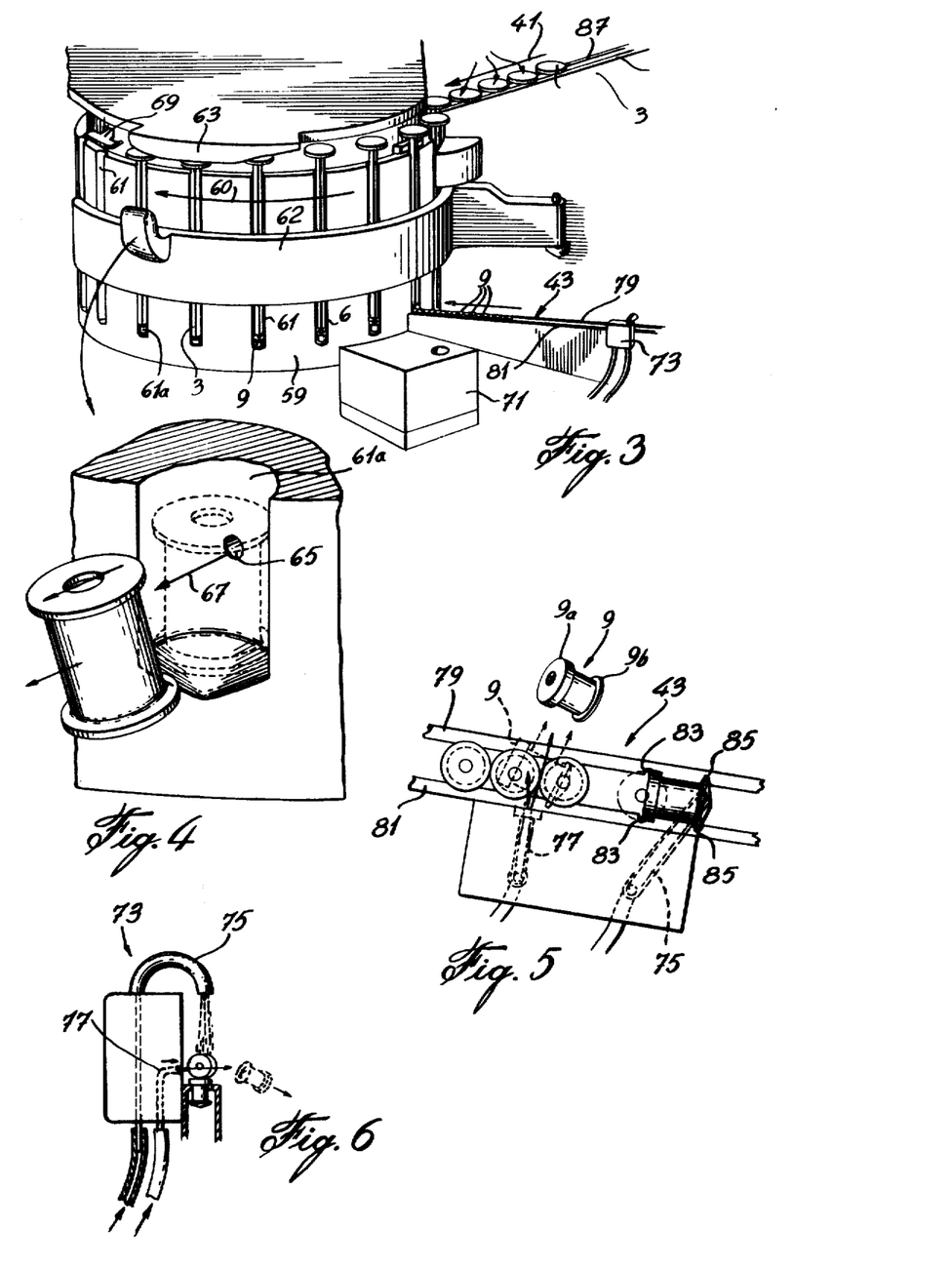
FIG. 3 is a three dimensional view of the sub-assembly station.
FIGS. 4, 5 and 6 illustrate features of the sub-assembly station.

Track 39 is disposed adjacent an upstream slot 61 to feed the plungers one at a time to the sub-assembly station, and track 43 is disposed adjacent a slot downstream of track 41 to feed the plunger tips, one at a time, to the bottom ends of the slots 61.

Cam 63 is disposed, in stationary arrangement, over the top of the rotating drum 59 and downstream of the tracks 39 and 43. The purpose of the cam is to assemble the plunger stem and the plunger tip as will be described below. Ejecting means 65 is disposed in the bottom end of slot 61a just downstream of cam 63. As can be seen in FIG. 4, the means 65 comprises an airhole which is connected to a source of air under pressure providing an airstream in the direction of arrow 67. Safety switch 69 is located over the slot downstream of slot 61a and photo detector means 71 is located adjacent track 43.

Airblower 73 is mounted on track 43 as can be seen in FIG. 3. As seen in FIGS. 5 and 6, the airblower consists of pipe 75 which provides a vertically downward stream of air, and pipe 77 which provides a lateral air stream.

Means for orienting tips 9 are included on track 43. As can be seen in FIG. 5, the ends of the tips 9 include a thick flange 9a and a thin flange 9b. Proper orientation for the tip is with the thick flange 9a in the upward direction. The orienting means for the tips includes rails 79 and 81 on track 43, the rails being spaced by a distance greater than the diameter of the central part of the tip but less than the diameter of the flanged portions thereof. The orienting means also includes notch pairs 83 and 85 which provide openings large enough to permit flanges 9b to pass therethrough, but small enough to prevent flanges 9a from passing. Thus, as a tip passes over the notches, the thin flange 9b will fall through the notches, and the thick flange 9a will ride the rails.

As the tips are relatively light weight, the force of gravity alone is not enough to pull the tip down into its oriented position. For this reason, pipe 75 is disposed over the notch pairs 83 and 85, and the vertically downwardly air stream provides a force to push the tip down into its oriented position.

In some cases, the tips will be riding the rails in such a fashion that the flanges 9b will not fall into the notch pairs. An example of this is illustrated in dotted lines in FIG. 5. Such tips must be pushed off the track before they reach the sub-assembly station or else they will enter the sub-assembly station in an unoriented condition. To accomplish this, pipe 77 provides a lateral air stream which will blow off the rails any tips which are riding the rails. The tips will be blown into a container which is not shown in the drawings.

Photo detector 71 is provided to detect a lack of plunger tips at the front end of the track 43. Such a lack could be caused by a jam up further up on the track or a stock out of parts. In any case, if any part is not arriving at the apparatus, the entire apparatus must be stopped to avoid assemblying syringes with a deficiency of parts. A source of light (not shown) is located on the other side of the track from the detector 71, and rays of light from the source will be blocked by plunger tips when there are tips in the track. When there are no tips, the rays of light will pass to the detector and activate the detector. The output of the detector is connected to the source of power for the apparatus and will operate to cut the power off, and thereby stop the apparatus, when it detects light.

The light rays will be directed at the bottom end of the tip so that if a tip which is riding the rails should somehow pass pipe 77 and not be blown off the rails, when it arrives adjacent the detector, it will not block the ray of light and prevent it from reaching the detector. Thus, under this condition, the apparatus will also be stopped.

To properly orient the plungers, track 43 is provided with rails 87 and 89. As can be seen, the spacing between the rails 87 and 89 is greater than the diameter of the longitudinal portion of the stem, but less than the diameter of the flanged portion thereof. Thus, the longitudinal portion will fall between the rails by the force of gravity, whereas the flanged portion will be caught by the rails and will ride on the rails along the track.

Figure 7:
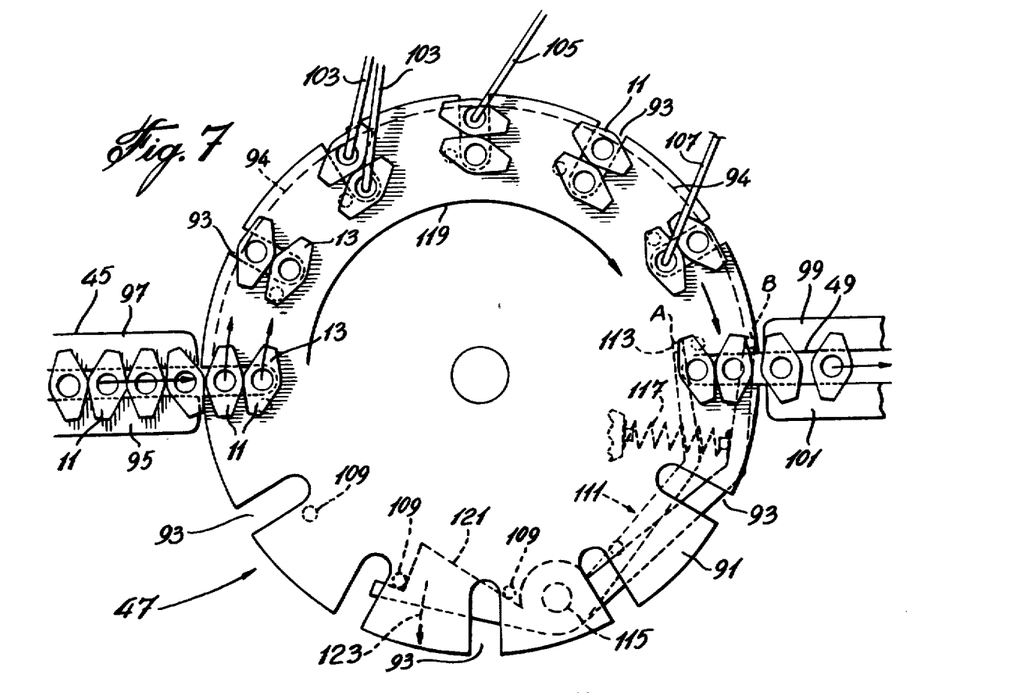
FIG. 7 is a top view of the processing station.

The cleansing and coating station is shown, in somewhat schematic form, in FIG. 7 of the drawings. As seen in FIG. 7, this station includes wheel 91 having a plurality of equally spaced notches 93. Each notch is long enough to receive two barrels in side by side position, and guide 94 insures that the barrels are retained at the closed end of the notches. The width of each notch is greater than the diameter of the main portion of the barrel, but smaller than the smallest dimension of the flange 13 thereof.

As seen in both FIGS. 2 and 7, station 47 is fed from track 45 and, in turn, feeds track 49. Tracks 45 and 49 comprise orienting means for the barrels which consist of, respectively, rails 95 and 97 on track 45 and rails 99 and 101 on track 49. Again, the respective rails are separated by a distance greater than the diameter of the main portion of the barrels but less than the smallest dimension of the flange 13 thereof.

The wheel 91 is rotated by means well known in the art, in the direction of arrow 119, in a start-stop, indexed manner and moves in each indexed step through a distance equal to the distance between adjacent notches 93.

Disposed above the wheel 91 at a distance equal to two indexed steps from track 45, are air hoses 103. The air hoses are connected to a source of pressurized air (not shown) and are adapted to be lowered into the tubes of their adjacent barrels when the barrels are at rest in the position of the air hoses, and withdrawn after cleansing in reciprocating motion. the insides of the barrels are cleansed by the air blown through them.

The insides of the barrels are then lubricated with the use of pipes 105 and 107. Pipe 105 is one index step away from pipes 103, and pipe 107 is two index steps away from pipe 103. Pipes 105 and 107 are connected to a source of lubricant (not shown) such as silicone, and the pipes are adapted to be lowered into the tubes of adjacent barrels when the wheel is at rest, and withdrawn after lubrication in reciprocating motion. As the pipes are lowered, they spray lubricant on the inside surface of the tubes of the barrels. The lubricant is necessary to permit the plunger tips to slide easily in the barrel when the syringe is assembled.

When a slot 93 is adjacent track 49, it is necessary to transfer the barrels in the slot to the track, and to this end, transer mechanism 111 is provided. As can be seen, the transfer mechanism comprises a pivot arm having an eject end 113. The arm is pivoted about pivot means 115, and is biased in a direction towards the outer periphery of wheel 91 by spring 117. Pins 109 are located on the downstream side of each slot 93. A camming surface 121 is located at the end of the pivot arm opposite the eject end thereof.

As wheel 91 rotates in the direction of arrow 119, pin 109 engages camming surface 121 to force the camming end of the pivot arm in the direction of arrow 123, so that the eject end of the pivot arm is pivoted towards the center of wheel 91. The camming action begins just after barrels have been ejected from a slot adjacent track 49, and as that slot begins to move away from the track. At the same time the slot just downstream of the track, which contains two barrels, begins to move towards the track.

As the wheel 91 continues to rotate, the camming end approaches the outer periphery of wheel 91 and the eject end reaches the position shown at A just as the filled slot is adjacent track 49. With the eject end in this position, the end of the pivot arm is on the side of the barrels opposite the track 49, i.e., it is behind the barrels relative to the position of the track.

When the filled slot moves into position directly opposite track 49, i.e., in a position to transfer its barrels to the track 49, the pin 109 slides over the edge of the cam 121 so that the camming end of the pivot arm is released. Because of the action of spring 117, the eject arm will be urged outwardly towards the outer periphery of wheel 91, pushing the barrels in the slot ahead of it and onto track 49. Thus, the barrels in the slot are transferred to the track 49.

Figure 8:
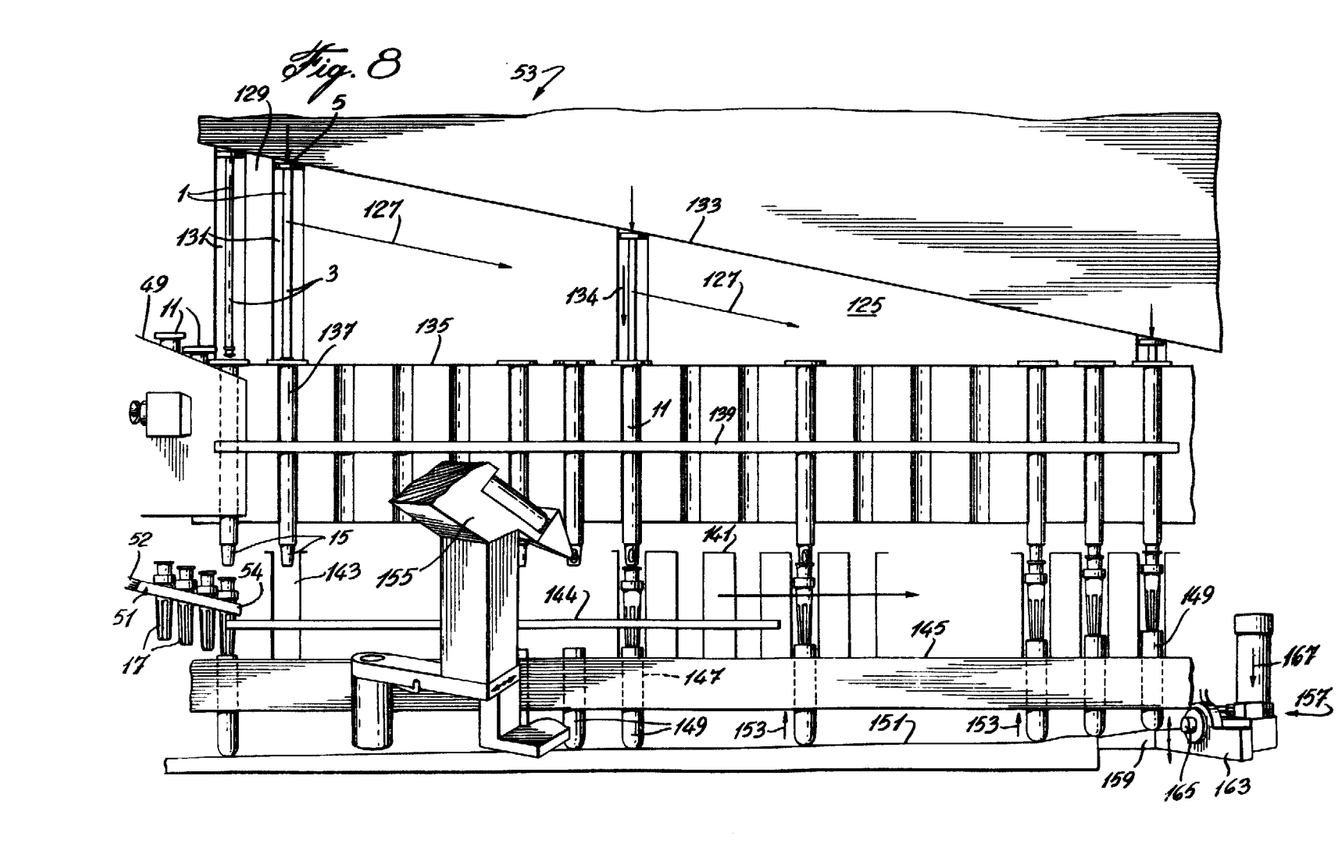
FIG. 8 is an unfolded view of the main assembly station.

Referring now to FIG. 8, the main assembly station 53 comprises a rotary drum 125 (which is shown unfolded for ease of illustration) having a plurality of carrying surfaces disposed along the height of the drum and around the periphery thereof. The drum rotates in the direction of the arrows 127.

The upper carrying surface 129, which rotates with the drum, comprises a plurality of open ended slots 131, equally spaced around the periphery of the drum, for receiving plungers 3 therein. Riding over the surface 129 is a camming surface 133 which engages the plunger tops 5 to force the plungers downwardly in the direction of the arrows 134 as the drum rotates. As will be appreciated, the camming surface is fixed relative to the motion of the surface 129.

Moving together with surface 129 as the drum rotates is center surface 135. Surface 135 comprises a plurality of open end slots 137, equal in number to and aligned with respective ones of slots 131. The slots 137 carry barrels 11, and guide 139 restrains the barrels in the slots and prevents them from falling out of the slots.

Disposed below center surface 135 is lower surface 141 which includes a plurality of open ended slots 143. Slots 143 are equal in number to and aligned with respective ones of slots 137 and the slots receive needle arrangements 17 therein. Guide 144 restrains the arrangements 17 in the slots 143.

Push rod carrying surface 145 is disposed below the surface 141 and includes a plurality of cylindrical openings 147, each of which contains a push rod 149 which is slidable up and down in its respective opening. Openings 147 are equal in number to and aligned with respective ones of slots 143. The bottom ends of the push rods 149 ride on camming surface 151 so that the push rods are pushed upwardly in the direction of arrow 152 as surface 145 rotates with the drum. As will be clear, the camming surface 151 is fixed relative to the motion of the drum, while surface 141 rotates with the drum, so that the needle arrangements 17 are forced upwardly in the direction of the arrow 153 as the drum rotates.

Glue dispensor 155 dispenses glue on the needle receiving end 15 of the barrel 11 so that, as the needle arrangement 17 is forced upwardly onto the barrel, the needle will be glued to the barrel. The glue dispensor preferably comprises a syringe whose plunger is actuated through a stroke of a fixed length each time glue is dispensed to insure the same quantity of glue on each barrel end. The plunger is returned to the end position after each stroke and the actuation of the plunger is synchronized with the appearance of an unglued barrel at the gluing station.

One of the requirements with respect to syringes is that the pressure applied while the needle arrangement is being fixed to the glued barrel be constant in all cases within a very narrow range of tolerance. However, it is possible that the parts of the syringe are not made to conform with very precise dimensional tolerances, so that the lengths of like parts can vary. Thus, it is necessary to provide means for applying constant pressure during the fixing process which can accommodate a range of different lengths of syringe parts. The means provided herein consist of constant pressure arrangement 157. As can be seen, the means 157 includes an arm 159 which is disposed in gap 161 of surface 151.

The arm 159 can be moved up and down so that the top surface of the arm 159 is alignable with the top surface of 151. the top surface of 159 will be cammed upwardly so that when the top surface of 159 is aligned with the top surface of 151, a continuous camming surface is provided before, through and after the gap 161.

Figure 9A:
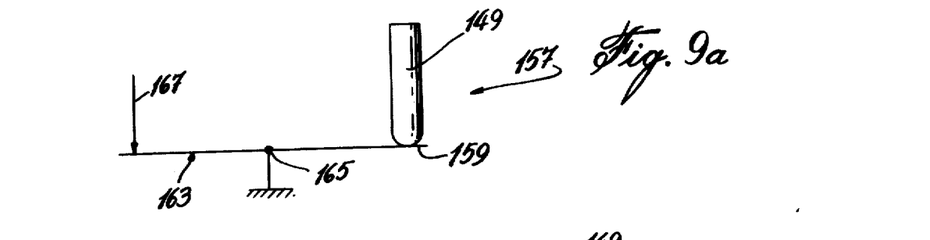
FIGS. 9a and 9b are schematic illustrations of an adjustable cam of the main assembly station.
Figure 9B:
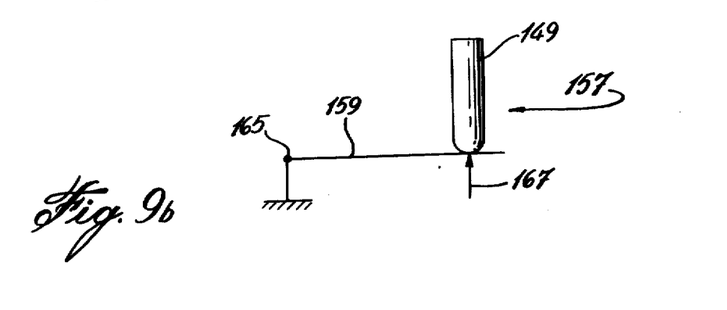

In order to provide constant pressure to each syringe which passes through the gap, the equalizing pressure arrangement comprises means as shown schematically in FIGS. 9a and 9b. As seen in FIG. 9a, the arm 159 comprises one arm of a lever whose other arm is labelled 163. The lever is pivoted about fixed point 165, and a constant pressure is applied in the direction of the arrow 167. The pressure can be applied by a coiled or other spring arrangement as is well known in the art, but is preferably applied by a hydraulic spring arrangement such as a piston and cylinder arrangement.

In the embodiment shown in FIG. 9b, the single arm 159 is pivotable about fixed point 165. The pressure is now applied under the arm 159 in the direction of the arrow 167. The same types of pressure sources can be used.

In operation, the apparatus works as follows, reference being had initially to FIG. 2 of the drawings:

Plungers 1 are fed from the container 25 to the hopper 27 and thence onto track 39 which carries them to sub-assembly station 41. At the same time, plungers tips 9 are fed, from container and hopper 29, onto the track 43 which similarly leads to sub-assembly station 41. Turning to FIG. 3, a separate plunger is disposed in a respective slot when the slot is adjacent the output end of the track 39. The plungers are held in an upward position in the slot to leave a gap between the bottom of the plunger and the bottom of the slot, and a plunger tip 9 is inserted in the gap when the slot reaches the output end of the track 43. The plungers and tips will have been properly oriented as above described.

Turning now to FIG. 3, as the drum 59 rotates in the direction of the arrow 60, the slot carrying the plunger and the plunger tip approaches the cam 63. The plunger tip receiving end will be forced into the longitudinal opening in the plunger tip when the plunger is forced downwardly by the action of the camming surface 63 on the flanged top surface of the plunger. Thus, after the slot has passed the cam 63, the plunger tip in that slot is firmly mounted on the plunger at the plunger tip receiving end thereof.

Returning now to FIG. 2, the assembled plunger and plunger tip arrangement is fed to the backside of the drum 125 of assembly station 53. At the same time, the barrels 11, having been cleansed and lubricated at station 47, are fed to the drum on the other side of the drum via track 49, and needle arrangements 17 are fed to the drum, downstream of the barrel feeding location in the direction of rotation of the drum 125 as shown by the arrows 127 via track 51. The needle arrangements are oriented by rails 52 and 54 (see FIG. 8).

The plunger and tip arrangements are carried in slots 131 of upper carrying surface 129. Barrels 11 are inserted in slots 137 in center carrying surface 135 when the slots are adjacent the output end of the track 49, and needle arrangements are inserted in slots 143 of lower carrying surface 141 when the slots are adjacent the output end of track 51.

Camming surface 133 begins to slope downwardly downstream of track 49 so that when the plunger and tip arrangements are pushed down by the camming surface 133, there will be a barrel in the slot below each plunger and tip arrangement, and the plunger and tip arrangement will be driven into its respective barrel.

Surface 151 slopes upwardly downstream of the gluing station to mount the needle arrangement 17 onto the bottom end of the barrel, and the correct pressure is applied at the constant pressure arrangement, to provide a completely assembled syringe. The assembled syringes are carried on track 55 (see FIG. 2) and deposited in the container or ramp 57.

As will be appreciated, when the apparatus is in operation, all slots in all drums will be filled with their appropriate elements between the input portion for these elements and the output portion of the drum. The apparatus is in continuous motion except for the station 47 and assembly of the syringes, or sub-assemblies thereof, is completed on a continuous basis.

Although a specific embodiment has been described and discussed above, this was the purpose of illustrating, but not limiting, the invention. Various modifications, which will come readily to the mind of one skilled in the art, are within the scope of the invention as defined in the appended claims.

I claim:

1. An apparatus for automatically assembling syringes, each said syringe comprising; a plunger having a stem, a top flanged end, and a bottom tip receiving end; a tip for mounting on said tip receiving end; a cylindrical barrel having a top flanged end and a bottom needle arrangement receiving end, said barrel receiving said plunger and tip in the interior thereof; and a needle arrangement for mounting on said needle arrangement receiving end;

said apparatus comprising;

a sub-assembly station for mounting said tip on said plunger including a first rotary drum having a plurality of equally spaced vertical slots disposed around the periphery thereof, each said slot being open at the top end thereof and closed at the bottom end thereof, means for rotating said drum in a first direction, means for providing plungers to said drum to be inserted at the top ends of respective slots one at a time, said plungers being inserted in said slots with the top ends of said plungers being adjacent the top ends of the respective slots and the plunger stems extending downward in the slot, a gap being provided in said slot between the tip receiving end and the bottom of each respective slot, means disposed downstream in said first direction of said means for providing plungers, for providing tips in the gaps at the bottom ends of the slots one at a time, a camming surface disposed downstream, in said first direction of said means for providing tips, and located at the top end of said drum to engage the flanged top ends of the plungers as the drum rotates in said first direction, said cammed surface being sloped downwardly in the first direction, whereby the plungers are forced downwardly as they pass the camming surface, to force the tip receiving ends into the tips to mount the tips on the plunger and provide a plunger and tip arrangement;

a processing station for cleansing and lubricating said barrels comprising elongated first means connected to a source of cleansor, said elongated first means being movable by vertically upwardly and vertically downwardly first moving means, elongated second means connected to a source of lubricant, said elongated second means being movable by vertically upwardly and vertically downwardly second moving means, and stop and start moving means to moving said barrels to said processing station such that one barrel is disposed under said elongated first means and another barrel is disposed under said elongated second means during each stop condition, whereby, during each stop condition the elongated first means is inserted in said one barrel and withdrawn from said one barrel cleansing said one barrel during the insertion and withdrawal of said elongated first means, said elongated first means being inserted in said one barrel after the start of a stop condition and being withdrawn from said one barrel before the start of the following start condition and whereby, during each stop condition the elongated second means is inserted in said other barrel and withdrawn from said other barrel lubricating said other barrel during the insertion and withdrawal of said elongated second means, said elongated second means, said elongated second means being inserted in said other barrel after the start of a stop condition and being withdrawn from said other barrel before the start of the following start condition;

a main assembly station for assembling the plunger and tip arrangements, the processed barrels and the needle arrangement comprising; a second rotary drum having means for rotating said drum in an assembly direction; said second rotary drum having an upper carrying surface for receiving plunger and tip arrangements from said sub-assembly station at a first point on said second rotary drum, said upper carrying surface being movable with said second rotary drum and comprising a plurality of equally spaced vertical plunger and tip arrangement carrying slots disposed around the periphery of said second rotary drum; an upper camming surface disposed over the top of said upper carrying surface and sloping downward in said assembly direction, said upper camming surface being fixed relative to the motion of said second rotary drum, said upper camming surface engaging the top flanged ends as said upper surface moves past the upper camming surface in the assembly direction whereby to force the plunger and tip arrangements downwardly; a center carrying surface for receiving processed barrels from said processing station at a second point on said second rotary drum downstream of said first point, said center surface comprising a plurality of equally spaced vertical barrel carrying slots disposed around the periphery of the second rotary drum, said center carrying surface being movable with said second rotary drum; a lower carrying surface for receiving said needle arrangements at a third point on said second rotary drum downstream of said second point, said lower carrying surface comprising a plurality of vertical needle arrangement carrying slots disposed around the periphery of said second rotary drum, said lower surface being movable with said second rotary drum;

the plurality of said vertical plunger and tip arrangement slots being equal to and aligned with respective ones of the plurality of vertical barrel carrying slots and the plurality of needle arrangement carrying slots;

glue dispensor means located adjacent said second rotary drum at a fourth point thereof downstream of said third point, for applying glue to each needle arrangement receiving end of each barrel as each barrel reaches said fourth point;

a rod carrying means disposed around the periphery of said second rotary drum and beneath said carrying surface and movable with said second rotary drum, said rod carrying means comprising a plurality of vertical rods movable up and down in said rod carrying means, the plurality of rods being equal to and aligned with respective ones of the plurality of needle arrangement carrying slots;

a lower camming surface disposed below said rod carrying means and sloping upward in said assembly direction, the lower carrying surface being fixed relative to the motion of said second rotary drum, the lower camming surface engaging the bottom ends of said rods to force said rods upwardly;

the top end of said rods engaging the bottom ends of respective ones of said needle arrangement, whereby the needle arrangements are forced upwardly as the rods are forced upwardly;

constant pressure applying means in said lower camming surface disposed downstream of said glue dispensor means and adapted to apply constant pressure, through each said rods, to a respective needle arrangement, as it is being mounted on a respective barrel;

whereby, as said second rotary drum moves in the assembly direction each plunger and tip is inserted into a respective processed barrel, glue is applied to each barrel at the needle arrangement receiving end thereof, each needle arrangement is mounted on a respective barrel at the glued needle receiving end thereof, and constant pressure is applied to each needle receiving end to fix it to its respective barrel, to provide completely assembled syringes.

2. An apparatus as defined in claim 1 and further comprising;
- a first container for said plungers;
- a second container for said plunger tips;
- a third container for said barrels;
- a fourth container for said needle arrangement;
- a first track for carrying said plungers to said sub-assembly station at one point therof, said first track comprising rails for orienting said plungers in a vertical attitude with the flanged ends at the top;
- a second track for carrying said plunger tips to said sub-assembly station downstream of said one point thereof, said second track comprising rails for orienting said plunger tips;
- a third track for carrying said barrels to said processing station, and a fourth track for carrying processed barrels to the second point on said second rotary drum, said third and fourth tracks comprising rails for orienting said barrels in a vertical attitude with the flanged ends thereof at the top; and
- a fifth track for carrying said needle arrangements to the third point on said second rotary drum, said fifth track comprising rails for orienting said needle arrangements.

3. An apparatus as defined in claim 2 wherein each said tips comprises a flange at both ends thereof, one of each said flanges being a wide flange and the other one of each said flanges being a narrow flange, and wherein the rails on said second track comprise;
- a first pair of notches wide enough to pass the narrow flanges but not the wide flanges;
- a second pair of notches wide enough to pass the wide flanges;
- the first pair of notches being spaced from the second pair of notches by a distance substantially equal to the length of the tips;
- a first source of pressurized air to provide a vertically downwardly directed steam of air disposed over the track adjacent the first pair of notches; and
- a second source of pressurized air, downstream of said first source to provide a steam of air across said second track.

* * * * *